(12) United States Patent
Koo et al.

(10) Patent No.: US 9,594,041 B2
(45) Date of Patent: Mar. 14, 2017

(54) CAPACITIVE HUMIDITY SENSOR

(71) Applicant: MagnaChip Semiconductor, Ltd., Cheongju-si (KR)

(72) Inventors: Sang Geun Koo, Cheongju-si (KR); Kwan Soo Kim, Cheongju-si (KR)

(73) Assignee: Magnachip Semiconductor, Ltd., Cheongju-si (KR)

( * ) Notice: Subject to any disclaimer, the term of this patent is extended or adjusted under 35 U.S.C. 154(b) by 251 days.

(21) Appl. No.: 14/188,019

(22) Filed: Feb. 24, 2014

(65) Prior Publication Data
US 2015/0068302 A1 Mar. 12, 2015

(30) Foreign Application Priority Data
Sep. 6, 2013 (KR) .................. 10-2013-0107394

(51) Int. Cl.
*G01N 27/22* (2006.01)
*H01G 7/00* (2006.01)
*G01R 27/26* (2006.01)

(52) U.S. Cl.
CPC ........... *G01N 27/223* (2013.01); *G01N 27/22* (2013.01); *G01R 27/26* (2013.01); *H01G 7/00* (2013.01)

(58) Field of Classification Search
CPC . C07C 2101/14; C07C 233/22; C07C 233/60; C07C 235/34; C07C 235/60; C07C 235/78; C07C 237/20; C07C 237/30; C07C 237/44; C07C 245/08; C07C 317/44; C07D 207/20; C07D 207/337; C07D 209/28; G01N 27/223; G01R 27/2605

USPC ....................................................... 73/335.04
See application file for complete search history.

(56) References Cited

U.S. PATENT DOCUMENTS

| | | | |
|---|---|---|---|
| 5,583,359 A * | 12/1996 | Ng ...................... | H01L 23/5223 257/306 |
| 6,690,569 B1 | 2/2004 | Mayer et al. | |
| 6,864,526 B2 * | 3/2005 | Inbe ....................... | H01L 21/768 257/295 |
| 7,009,832 B1 * | 3/2006 | Chen ....................... | H01G 4/228 257/306 |
| 7,126,809 B2 * | 10/2006 | Iioka .................... | H01L 23/5223 257/532 |
| 7,209,340 B2 * | 4/2007 | Iioka .................... | H01L 23/5223 257/532 |
| 7,541,254 B2 * | 6/2009 | Lee ........................ | H01L 27/016 257/308 |
| 7,594,435 B2 | 9/2009 | Sudo | |
| 8,707,781 B2 * | 4/2014 | Humbert .............. | G01N 27/223 324/689 |
| 2003/0179805 A1* | 9/2003 | Hamamoto .......... | G01N 27/225 374/16 |
| 2009/0009193 A1* | 1/2009 | Hsiung ................ | G01N 27/223 324/664 |
| 2011/0146400 A1* | 6/2011 | Humbert .............. | G01N 27/223 73/335.04 |

(Continued)

*Primary Examiner* — John Fitzgerald
*Assistant Examiner* — Gedeon M Kidanu
(74) *Attorney, Agent, or Firm* — NSIP Law (57) ABSTRACT

Provided is a capacitive humidity sensor. The capacitive humidity sensor includes an upper electrode disposed on a first plane, a plurality of first electrodes included in the upper electrode, a plurality of second electrodes disposed between the first electrodes, and a humidity sensitive layer surrounding the second electrodes.

20 Claims, 10 Drawing Sheets

(56) References Cited

U.S. PATENT DOCUMENTS

| | | | | |
|---|---|---|---|---|
| 2011/0185810 A1* | 8/2011 | Humbert | ............ | G01N 27/223 |
| | | | | 73/335.04 |
| 2011/0259099 A1* | 10/2011 | Hong | ................ | G01N 27/223 |
| | | | | 73/335.04 |
| 2012/0151726 A1* | 6/2012 | Chung | ................ | H01G 4/228 |
| | | | | 29/25.41 |
| 2014/0035146 A1* | 2/2014 | Kim | .................. | H01L 23/485 |
| | | | | 257/760 |

* cited by examiner

CAPACITIVE HUMIDITY SENSOR

CROSS-REFERENCE TO RELATED APPLICATIONS

This application claims the benefit under 35 USC 119(a) of Korean Patent Application No. 10-2013-0107394 filed on Sep. 6, 2013, in the Korean Intellectual Property Office, the entire disclosure of which is incorporated herein by reference for all purposes.

BACKGROUND

1. Field

The following description relates to a capacitive humidity sensor, and to capacitive humidity sensor that minimizes a humidity sensitive area by increasing a variation of capacitance according to a humidity change to improve sensitivity.

2. Description of Related Art

A humidity sensor is a sensor that detects a level of humidity based on an electrical signal that changes its value with a change of humidity. A humidity sensor may accurately sense the humidity level by determining a change in an electrical property of a humidity sensitive material due to moisture.

Humidity sensors may be divided into resistive humidity sensors and capacitive humidity sensors. Humidity sensors are widely used to maintain automobiles, medical devices, air purification systems, automatic cooling/heating systems, home appliances, mobile devices and the like in an optimal state.

A resistive humidity sensor measures humidity based on a change in resistance that is changed by humidity. Resistive humidity sensors are widely used because resistance humidity sensors tend to be price competitive in comparison to capacitive humidity sensors.

However, recently, capacitive humidity sensors are manufactured on a semiconductor substrate in a one-chip form. Accordingly, it may be possible to obtain capacitive humidity sensors that are more price competitive than resistive humidity sensors. As a result, the use of capacitive humidity sensors is increasing.

Further, capacitive humidity sensors may exhibit higher reliability, and may exhibit more linear sensor features and low influences due to a temperature, in comparison to resistive humidity sensors. A capacitive humidity sensor may operate as a capacitor type device having a humidity sensitive material such as polymer or ceramic absorbs moisture, which has permittivity that is changed in the presence of moisture. That is, a humidity sensitive layer for sensing humidity may be present inside the device, and the permittivity of the humidity sensitive layer may change when moisture is introduced through the humidity sensitive layer. As a result, the capacitance is changed, and the capacitance may be determined to determine a level of humidity.

An example of a capacitive humidity sensor for sensing humidity is disclosed in U.S. Pat. No. 6,690,569 (Capacitive Sensor).

Referring to U.S. Pat. No. 6,690,569, the humidity sensitive material is filled between different electrodes to form a measuring layer.

Therefore, when a potential difference is applied to both ends of the electrode, an electric field is formed around the electrode. For instance, the largest electric field is formed in a space between electrodes having different potentials and facing each other.

However, in the capacitive humidity sensor, since moisture cannot penetrate a substrate below an electrode, a variation of permittivity is not changed. Therefore, a variation of the capacitance is limited.

Further, in a device in which a single conductive layer is used as the electrode, an electrode height is limited depending on a process capacity. Then, a dimension in which the electrodes overlap with each other decreases, and as a result, a variation of the capacitance depending on a humidity change is limited.

As such, as the variation of the capacitance is limited, sensitivity is reduced, deteriorating the sensing characteristics and response characteristics of the capacitive humidity sensor.

Accordingly, in order to maintain the sensitivity of the capacitive humidity sensor, an area occupied by a dielectric material needs to be secured to some degree. The dielectric material maybe a humidity sensitive material having a property in which permittivity is changed depending on moisture content. However, in order to increase the area occupied by the dielectric material, the size of the sensor cannot be reduced more than the area needed for the dielectric material. As a result, devices and products in which the sensor may be installed are limited due to the size of the sensor.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a capacitive humidity sensor includes an upper electrode disposed on a first plane, a plurality of first electrodes included in the upper electrode, a plurality of second electrodes disposed between the first electrodes, and a humidity sensitive layer surrounding the second electrodes.

The first electrodes may be connected to each other on the first plane, and the second electrodes may be separated from each other on the first plane.

The general aspect of the capacitive humidity sensor may further include a lower electrode disposed on a second plane below the first plane.

The humidity sensitive layer may be filled in a groove disposed deeper than a bottom surface of the upper electrode.

The capacitive humidity sensor may further include a pad region including a first pad connected to the first electrode and a second pad connected to the second electrode.

An electrode protection layer may be disposed on an upper surface of the upper electrode.

The upper surface of the upper electrode may have a curved shape.

The general aspect of the capacitive humidity sensor may further include a first via connecting at least one of the second electrodes and the lower electrode.

The general aspect of the capacitive humidity sensor may further include a second via that connects to at least one of the first electrodes.

A depth of the first via may be different from a depth of the second via.

The general aspect of the capacitive humidity sensor may include a dummy electrode that extends from at least one of the first electrodes and positioned between two adjacent second electrodes.

In another general aspect, there is provided a capacitive humidity sensor including an upper interconnection disposed on a first plane, a lower interconnection disposed on a second plane, a first electrode and a second electrode included in the upper interconnection, a lower electrode included in the lower interconnection and connects to the second electrode, and a humidity sensitive layer surrounding the second electrode.

A depth of the humidity sensitive layer may be smaller than a depth of the first plane.

Upper surfaces of the first electrode and the second electrode may be curved surfaces.

The depth of the humidity sensitive layer may be positioned between the first plane and the second plane.

In another general aspect, a capacitive humidity sensor includes an upper electrode disposed on a first plane and comprising two or more first electrodes disposed parallel to each other, a plurality of second electrodes disposed between two adjacent first electrodes and forming a role between the two adjacent first electrodes in the first plane, and a humidity sensitive layer disposed between the plurality of second electrodes and between the role of second electrodes and the two adjacent first electrodes.

The general aspect of the capacitive humidity sensor may further include a plurality of dummy electrodes protruding from the two adjacent first electrodes to be disposed between two adjacent second electrodes of the role of second electrodes.

The general aspect of the capacitive humidity sensor may further include a lower electrode disposed on a second plane below the first plane, and a plurality of vias connecting the plurality of second electrodes and the lower electrode.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness. The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Unless indicated otherwise, a statement that a first layer is "on" a second layer or a substrate is to be interpreted as covering both a case where the first layer is directly contacts the second layer or the substrate, and a case where one or more other layers are disposed between the first layer and the second layer or the substrate.

The spatially-relative expressions such as "below", "beneath", "lower", "above", "upper", and the like may be used to conveniently describe relationships of one device or elements with other devices or among elements. The spatially-relative expressions should be understood as encompassing the direction illustrated in the drawings, added with other directions of the device in use or operation. Further, the device may be oriented to other directions and accordingly, the interpretation of the spatially-relative expressions is based on the orientation.

Described below is an example of a capacitive humidity sensor that increases a variation of capacitance according to a change in humidity by providing various electrode array structures, generating an electric field even below an upper electrode, and using an electric field generated by a via connected to the upper electrode and a lower electrode.

Various examples of capacitive humidity sensors will be described in detail with reference to the accompanying drawings.

Here, when describing the examples according to the present disclosure, first, a layout of an upper electrode will be described through a plan view of one example of a capacitive humidity sensor.

Figure 1:
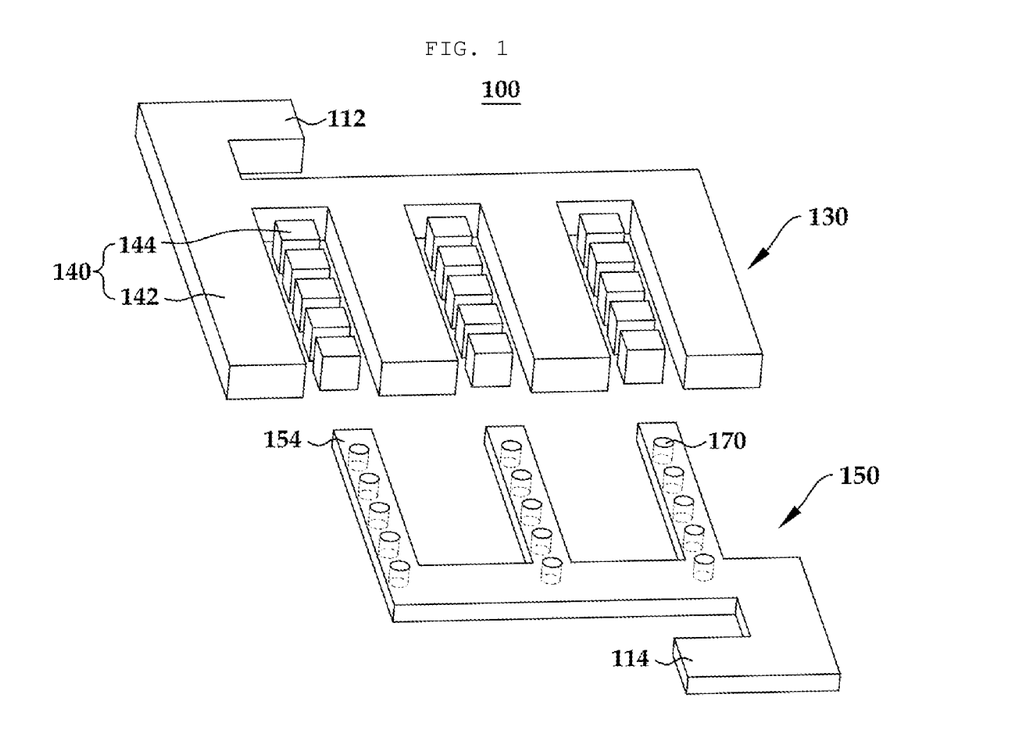
FIG. 1 is a schematic separate perspective view of an example of a capacitive humidity sensor.
Figure 2A:
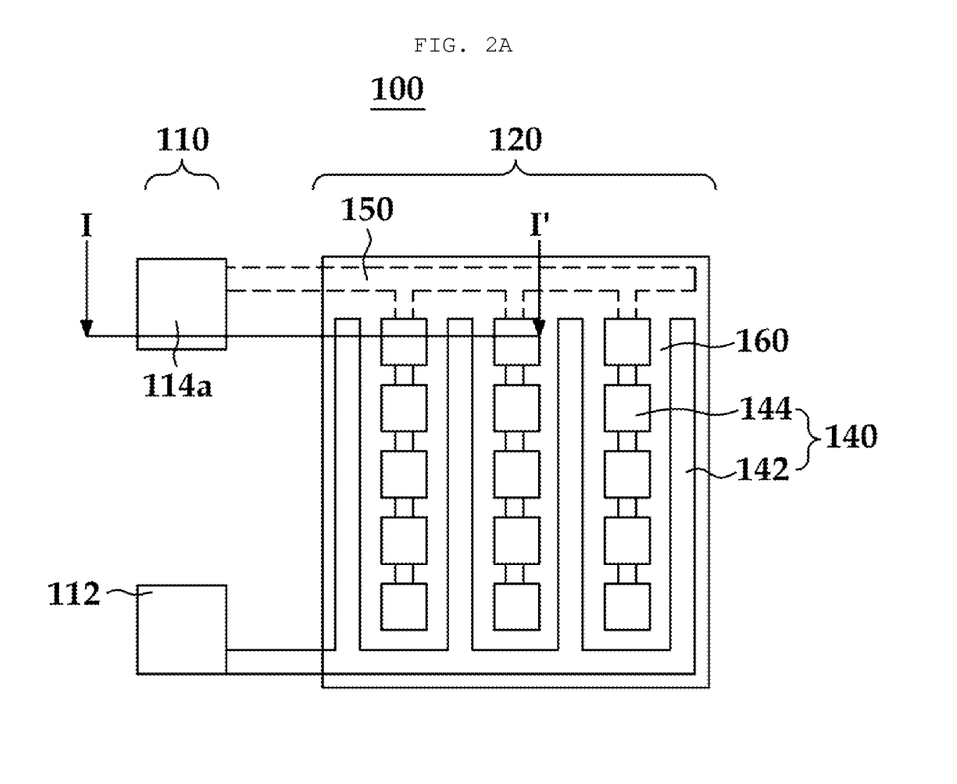
FIG. 2A is a plan view of the capacitive humidity sensor of FIG. 1.
Figure 2B:
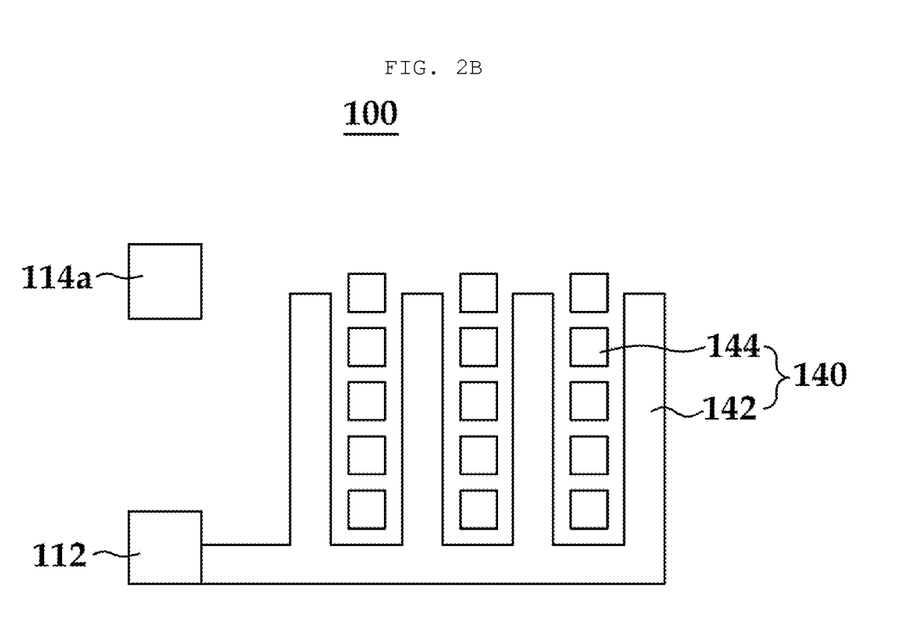
FIG. 2B is a plan view of an upper interconnection of the capacitive humidity sensor of FIG. 2A.
Figure 2C:
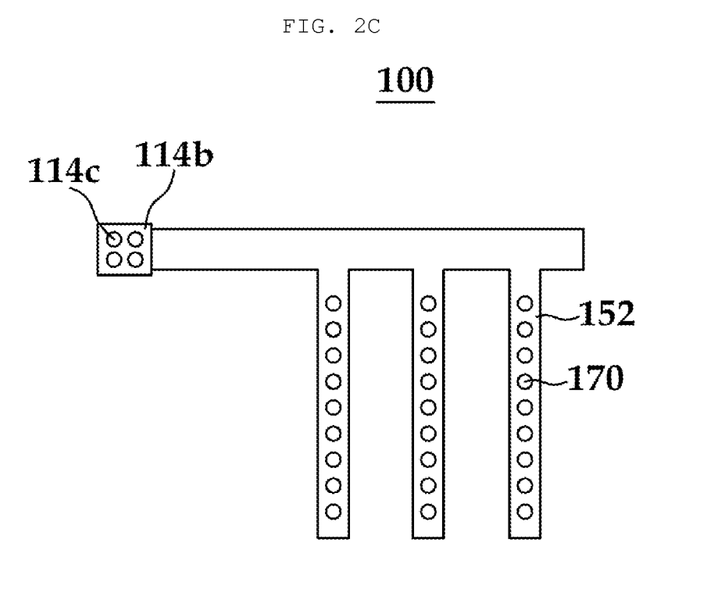
FIG. 2C is a plan view of a lower interconnection of the capacitive humidity sensor of FIG. 2A.
Figure 3:
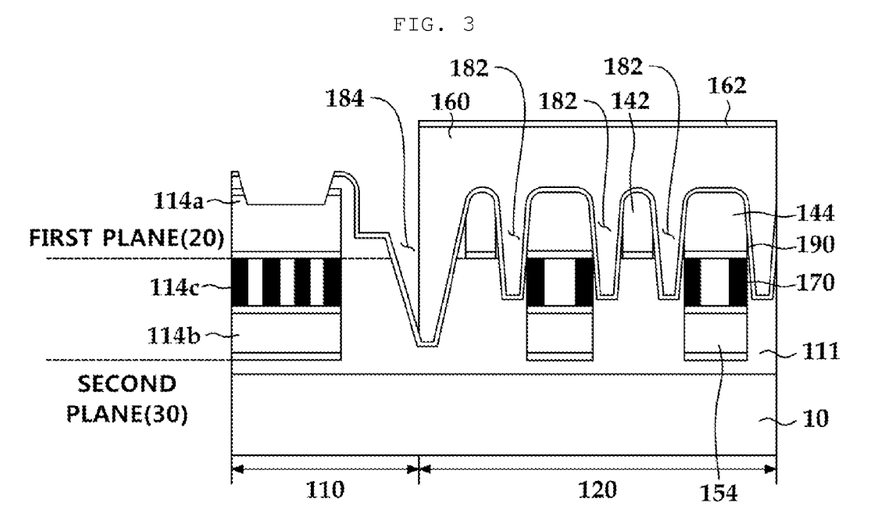
FIG. 3 is a cross-sectional view taken along line I-I' of FIG. 2A.

FIG. 1 is a schematic exploded perspective view of a capacitive humidity sensor according to a first example. FIG. 2A is a plan view of the example of the capacitive humidity sensor according to FIG. 1. FIG. 2B is a plan view of an upper interconnection illustrated in FIG. 2A. FIG. 2C is a plan view of a lower interconnection illustrated in FIG. 2A. FIG. 3 is a cross-sectional view taken along line I-I' of FIG. 2A.

First, referring to FIG. 1, a capacitive sensor 100 may be divided into an upper interconnection 130 and a lower interconnection 150. The upper interconnection 130 is positioned on a first plane, and the lower interconnection 150 is disposed on a second plane lower than the first plane. The first plane and the second plane are not the same surface.

The upper interconnection 130 is configured by an upper electrode 140 and a first pad 112. An empty space between the upper electrodes 140 is a region to form a humidity sensitive layer 160 (see FIG. 2A). The upper electrode 140 maybe divided into a first electrode 142 and a second electrode 144. Capacitance may be measured through the humidity sensitive layer between the first electrode 142 and the second electrode 144 by applying a (+) voltage to the first electrode 144 and a (−) voltage to the second electrode 144. The humidity sensitive layer is designed to be exposed to external air containing moisture. The first electrode 142 has a stripe shape, and a plurality of second electrodes 144 therebetween has a quadrangular shape. The first electrodes 142 are connected to each other, but the plurality of second electrodes 144 is separated from each other, and the humidity sensitive layer is disposed even between the second electrodes. The humidity sensitive layer surrounds each second electrode 144. In an existing structure, the second electrodes are attached to each other like the first electrodes. However, as in the illustrated sensor 100, when the plurality of second electrodes 144 are separated from each other, an area in which the second electrodes contact the humidity sensitive layer may be increased. As a result, sensitivity for a humidity change may be increased.

In addition, the lower interconnection 150 is configured by a lower electrode 154 and a second pad 114. A via 170 connecting the second electrode 144 of the upper interconnection 130 and the lower interconnection 150 is further included. As mentioned above, because the second electrodes 144 are separated from each other, the second electrodes 144 need to be connected to the lower interconnection 150. Accordingly, finally, the second electrode 144 formed in the upper interconnection 130 may be connected to the second pad 114 through the via 170.

Further, referring to FIG. 2, the capacitive humidity sensor 100 may be divided into a pad region 110 and a sensing region 120.

The pad region 110 is configured by a first pad 112 for the upper electrode and second pads 114a and 114b for the lower electrode. In this example, the second pads 114a and 114b are connected to each other through a via 114c. That is, the first pad 112 and the second pad 114a are positioned on the same plane, and the second pad 114b is positioned below the second pad 114a. The first pad 112 and the second pads 114a and 114b serve to connect the sensing region 120 and an external circuit (not illustrated) so as to transfer a signal sensed in the sensing region 120 to the external circuit.

The sensing region 120 includes electrodes and a humidity sensitive layer 160. The electrodes include upper electrodes 120, second electrodes 144, and lower electrodes 154. Both the upper electrodes 140 and the lower electrodes 154 need to be prepared with materials having free electron flow, and may be prepared by using anti-corrosive materials.

The upper electrodes 140 are divided into first electrodes 142 separated from each other and having a plurality of stripe shapes, and second electrodes 144 positioned between the first electrodes 142. The first electrodes 142 are connected to the first pad 112. The first electrodes 142 and the second electrodes 144 are separated from each other. As a result, an electric field may be generated between the first electrode 142 and the second electrode 144. In addition, in the example, the second electrode has a square shape. The reason is that a change in the capacitance may be more easily sensed by increasing an area of the second electrode 142 that contacts the humidity sensitive layer 160 disposed around the second electrode 142.

The lower electrode 154 is positioned below the second electrode 144. The lower electrode 154 has a size corresponding to the second electrode 144. In addition, the lower interconnection 150 connected to the second pad 114b is provided so that the lower electrode 154 may be positioned below the second electrode 144.

The humidity sensitive layer 160 is disposed between the first electrode 142 and the second electrode 144. In the one example, the humidity sensitive layer 160 uses a humidity sensitive material in which a dielectric constant is change according to relative humidity. As the humidity sensitive material, polymer, polyimide, and inorganic materials such as porous ceramics may be used. Such a humidity sensitive material has a characteristic of absorbing and discharging moisture according to relative humidity when the humidity sensitive material is exposed in air, and sensing the humidity is measuring a dielectric constant changed depending on a moisture content in the humidity sensitive material. Accordingly, the humidity sensitive layer 160 measures the change in humidity.

Next, referring to FIG. 3 showing the cross-sectional view taken along line I-I' of FIG. 2, a side structure of the capacitive humidity sensor will be described in more detail.

First, in FIG. 3, a bottom surface of the upper interconnection 130 is called the first plane 20 described above, and a bottom surface of the lower interconnection 150 is called the second plane 30.

Then, a semiconductor substrate 10 of the capacitive humidity sensor is formed. An insulating layer 111 is disposed on the substrate 10, and includes a pad region 110 at the left and a sensing region 120 at the right when viewed from the drawing.

In the pad region 110, second pads 114a and 114b are vertically formed, and a via 114c for connecting the pads is formed therebetween.

In the sensing region 120, first, a lower electrode 154 and a via 170 for connecting the electrodes are formed from the lower portion of the semiconductor substrate 10. At least one via 170 for connection with the second electrode 144 is formed. As such, when the second electrode 144 is interconnected downward by using the via, an effect that an area where the first electrode 142 and the second electrode 144 overlap with each other increases may be obtained.

In addition, the second electrode 144 is formed at an upper side corresponding to the lower electrode 154, and the first electrode 142 is formed at a side of the first electrode 144. The lower electrode is not required at a lower side of the first electrode 142.

A first groove 182 is formed between the first and second electrodes 142 and 144, and a second groove 184 is formed between the first electrode 142 and the pad region 110. The first groove 182 has a sufficient depth so that the humidity sensitive material is deposited deeper than the lower regions of the first and second electrodes 142 and 144. Accordingly, the first groove 182 may be positioned between the first and second electrodes 142 and 144 and the lower electrode 154, and may be deepened up to an area around or next to the lower electrode 154 when being more deeply etched. In this case, in order to ensure a larger humidity sensitive area, the humidity sensitive layer may be deposited by more deeply etching the first groove 182, but when the first groove 182 is etched up to the area around or next to the lower electrode 154, since the first groove 182 may influence a different electric property, for example, the insulating layer around the lower electrode 154 or contact the lower electrode 154, the first groove 182 may be positioned at least above the lower electrode 154. Meanwhile, since the second groove 184 does not influence the lower electrode 154, the second groove 184 may be formed deeper than the first groove 182. The second groove 184 is more deeply formed in order to increase an area of the second groove 184 which contacts the humidity sensitive layer 160. Of course, since the second groove 184 is deeply formed, the pad region 110 and the sensing region 120 may be more effectively separated from each other. As such, the depths of the first groove 182 and the second groove 184 may be different from each other due to a difference in pattern density.

In addition, according to one example, the first groove 182 and the second groove 184 are disposed deeper than the bottom surfaces of the first and second electrodes 142 and 144. The humidity sensitive material may be filled deeper than the bottom surfaces of the first and second electrodes 142 and 144. As such, when the humidity sensitive material exists up to the lower regions of the first electrode 142 and the second electrode 144 by the first groove 182 and the second groove 184, the humidity sensitive layer exists between the first electrode 142 and the second electrode 144. As a result, the humidity sensitive area increases, and the sensitivity of the capacitive sensor 100 increases. Accordingly, a variable width of the capacitance according to the humidity may increase in comparison to the capacitive humidity sensor mentioned in the related art.

Further, an electrode protection layer 190 may be formed on the surfaces of the first and second electrodes 142 and 144. In such an example, the electrode protection layer 190 prevents the electrodes from being corroded or oxidized by the moisture or the humidity sensitive material. If the electrode is deformed or the electric property thereof is changed due to corrosion or oxidization of the electrode, the sensing region 120 does not normally sense the humidity. Such an electrode protection layer may be formed by using oxides, nitrides, and oxynitrides. However, in an example in which the first and second electrodes 142 and 144 are manufactured with an anti-corrosive material, there is no concern of corrosion or oxidization. As a result, in such an example, the protection layer may not be formed.

The humidity sensitive layer 160 is formed inside of the first groove 182 and the second groove 184 and on the upper electrodes 142 and 144. To form the humidity sensitive layer 160, a humidity sensitive material that responds to changes in humidity is filled into the first groove 182 and the second groove 184, as described above. Such a humidity sensitive layer 160 may be formed in a single layer or a multi layer according to a manufacturing process.

In addition, a humidity sensitive layer protection layer 162 may be further formed on the humidity sensitive layer 160 to protect the humidity sensitive material. As the humidity sensitive layer protection layer 162, a material that reacts more sensitively to a change in capacitance may be used. For example, a membrane, polymer, porous ceramic, porous noble metal, porous oxide layer, and the like may be used to form the humidity sensitive layer protection layer 162. Porous materials may be used to allow a smooth flow of air containing moisture into the humidity protection layer 162.

Next, an example of a method of manufacturing a capacitive humidity sensor will be described.

FIGS. 4A-4H describe an example of a method of manufacturing the capacitive humidity sensor illustrated in FIG. 2A. In this example, some of generalized processes of the manufacturing method will be omitted for conciseness. Those skilled in art are capable of applying these generalized processes.

Figure 4A:
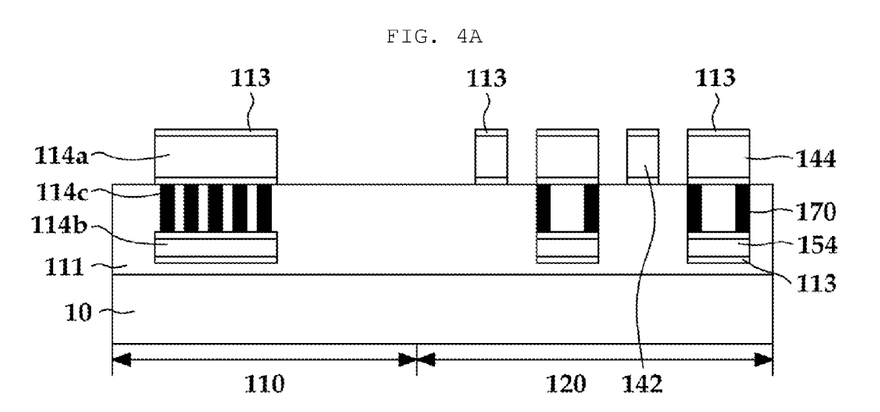
FIGS. 4A to 4H are cross-sectional views describing an example of a manufacturing process of a capacitive humidity sensor according to the embodiment illustrated in FIG. 1.

FIG. 4A illustrates a state in which the pad region 110, and the first electrode 142 and the second electrode 144 as the sensing region 120, are patterned on the semiconductor substrate 10. In this example, an insulating layer 111 exists on the top/bottom surfaces of the pad region 110, the first electrode 142, and the second electrode 144. The insulating layer 111 prevents an electric short phenomenon.

Figure 4B:
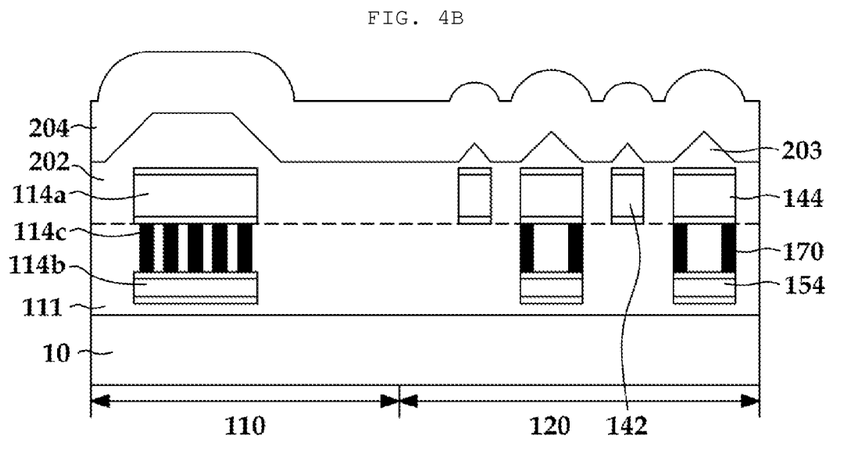

Referring to FIG. 4B, passivation layers 202 and 204 are formed. The passivation layers 202 and 204 may be formed as a HDP CVD oxide layer 202 or a nitride layer 204. In the example, two separate passivation layers 202 and 204 are deposited to more accurately pattern the first and second electrodes 142 and 144. That is, the upper portions of the first and second electrodes 142 and 144 are formed well in curved shapes 142a and 144a (see FIG. 4D) by an etching process as a subsequent process. As a result, in the passivation layers 202 and 204, regions 203 positioned directly on the first and second electrodes 142 and 144 are patterned in a substantially triangular shape. However, in other example, if desired patterning is possible, the patterning of the passivation layer is not performed twice, but may be performed only once.

Figure 4C:
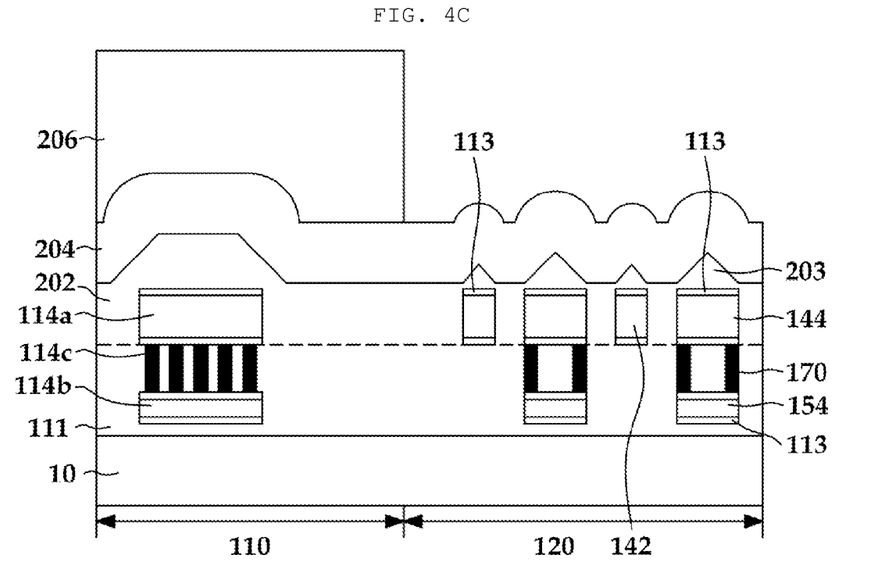

After the passivation layers 202 and 204 are formed as illustrated in FIG. 4C, the sensing region 120 is etched, and a photomask 206 is formed with a predetermined thickness in order to protect a region except for the sensing region 120.

Figure 4D:
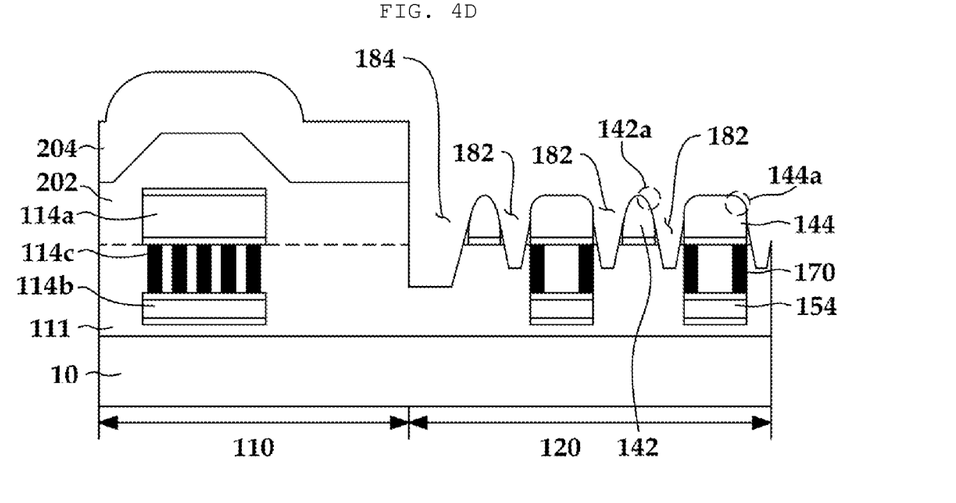

Thereafter, an etching process is performed. Then, the sensing region 120 corresponding to a region where the photomask 206 does not exist is etched. The etching process may be performed until the upper portions of the first electrode 142 and the second electrode 144 are formed in the curved shapes 142a and 144a while the passivation layers formed on the photomask 206 and the sensing region 120 are fully removed. The reason why the upper portions of the first electrode 142 and the second electrode 144 are formed in the curved shapes 142a and 144a is to prevent the electric field from being concentrated on only a predetermined region. Meanwhile, a space between the first electrode 142 and the second electrode 142, and a space between the first electrode 142 and the pad region 110 need to be sufficiently deeply etched so that the humidity sensitive material may be filled up to the lower regions of the electrodes. Accordingly, according to one etching process, the first groove 182 is formed between the first and second electrodes 142 and 144, and the second groove 182 is formed between the first electrode 142 and the pad region 110. The depths of the first groove 182 and the second groove 182 are different from each other. Such a state is illustrated in FIG. 4D. A portion of the passivation layer remains in the pad region 110, as illustrated in FIG. 4D.

Figure 4E:
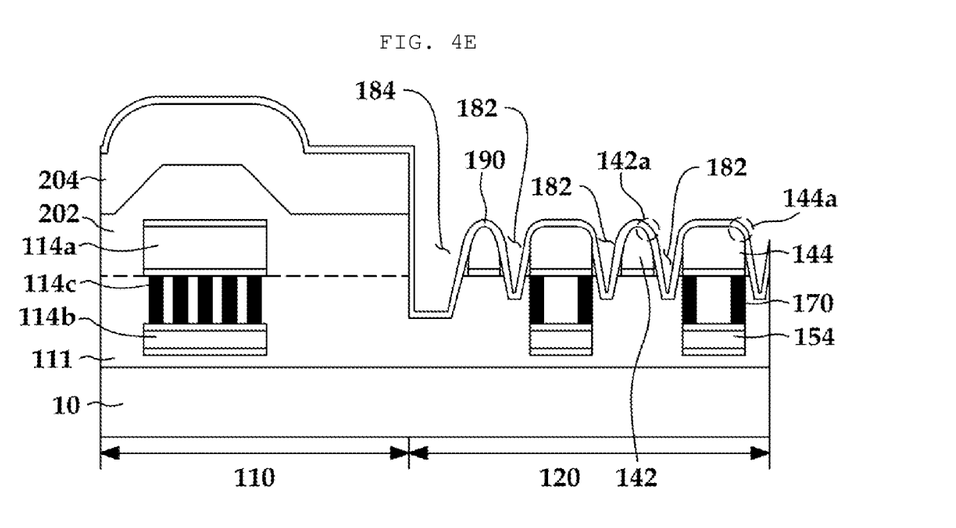
Figure 4F:
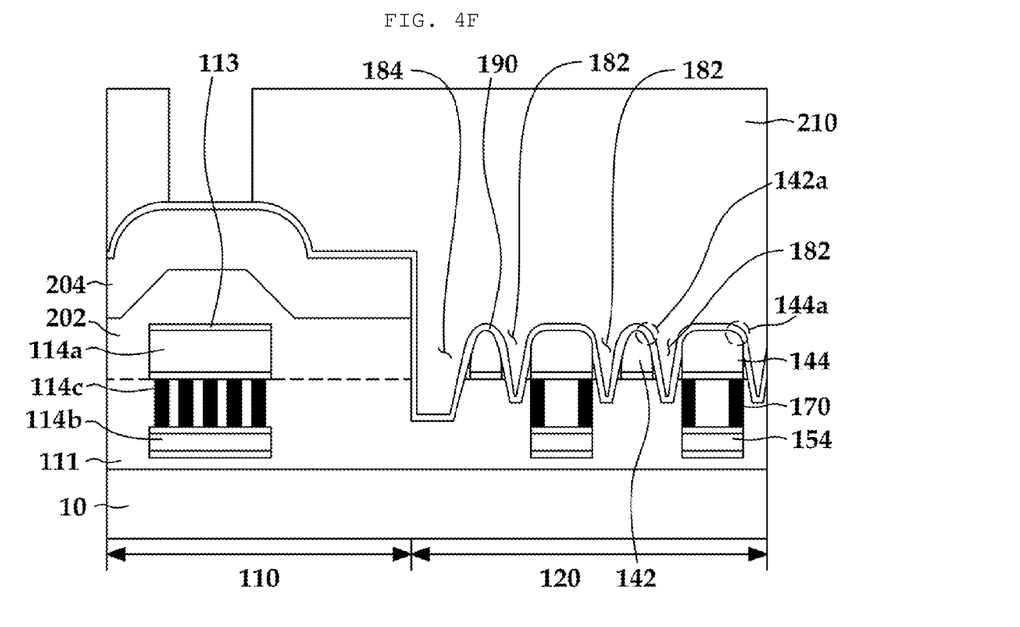

Next, as illustrated in FIG. 4E, the electrode protection layer 190 is deposited by a CVD method. The electrode protection layer 190 prevents corrosion of the upper portions of the first electrode 142 and the second electrode 144 that are exposed outside. In this case, the electrode protection layer 190 may be thinly formed so as to increase a variation rate of capacitance according to humidity. In other example, however, the electrode protection layer 190 need not be very thinly formed as thick as the electrode protection layer 190 cannot protect the electrode.

After the electrode protection layer 190 is deposited, the upper portion of the second pad 114a included in the pad region 110 needs to open so as to be connected with an external circuit. Accordingly, in the example illustrated in FIG. 4F, a mask 210 is patterned in the remaining region except for the region to form an opening in the pad region 110.

Figure 4G:
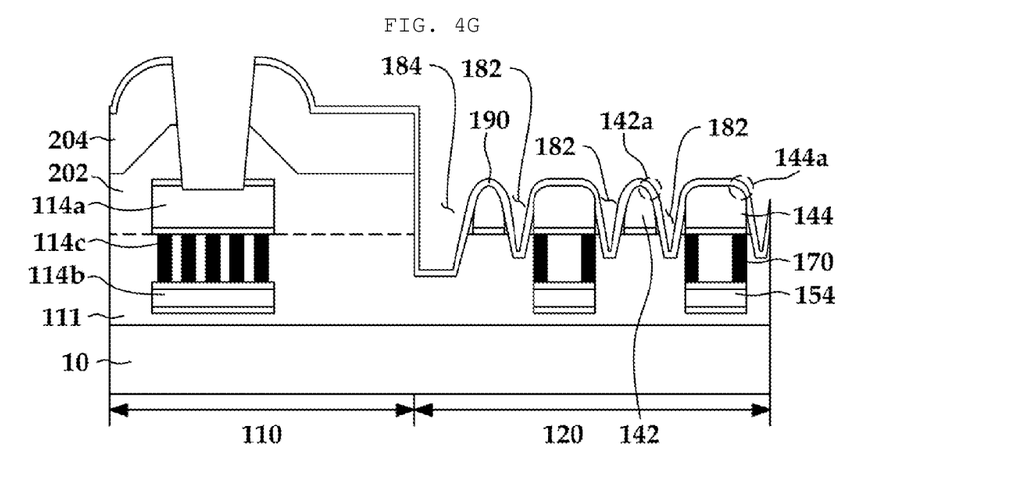

Thereafter, when the etching process is performed, as illustrated in FIG. 4G, the mask 210 is fully removed and thus a region of the top surface of the second pad 114a is exposed outside.

Figure 4H:
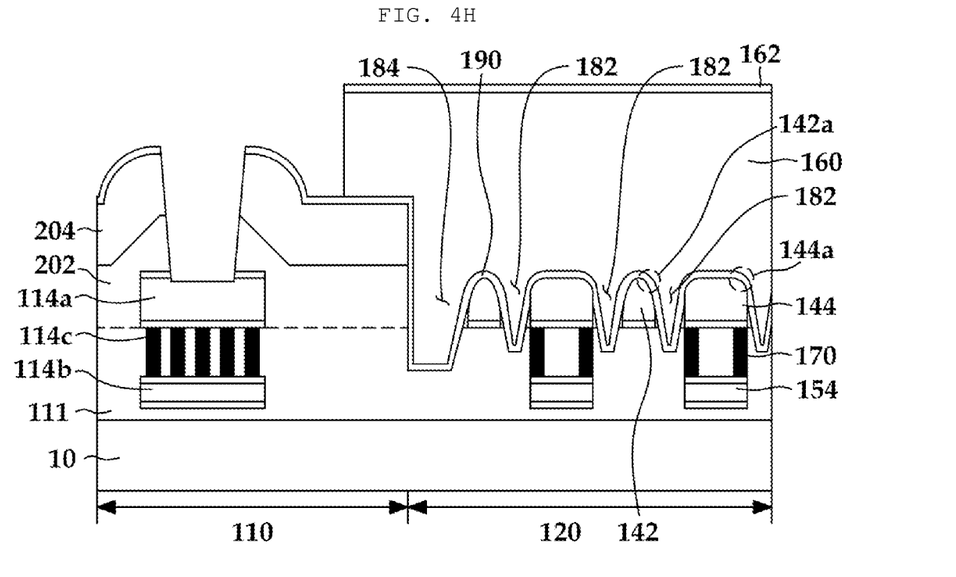

Thereafter, as illustrated in FIG. 4H, the humidity sensitive layer 160 is formed by coating the humidity sensitive material on the entire region of the sensing region 120, including the first groove 182 and the second groove 184. In this example, the humidity sensitive material may be formed in a single layer or formed in a multi layer through several processes.

Finally, the humidity sensitive material protection layer 162 for protecting the humidity sensitive material on the top surface of the humidity sensitive layer 160 may be formed. In addition, the humidity sensitive layer 160 included in the pad region 110 is removed through an additional photomask and etching process.

The capacitive humidity sensor completed by such a process may utilize the electric field formed below the electrodes because the humidity sensitive material is filled up to the lower regions of the electrodes.

Meanwhile, the present disclosure describes a structure that sufficiently ensures capacitance of a capacitive humidity sensor.

Figure 5:
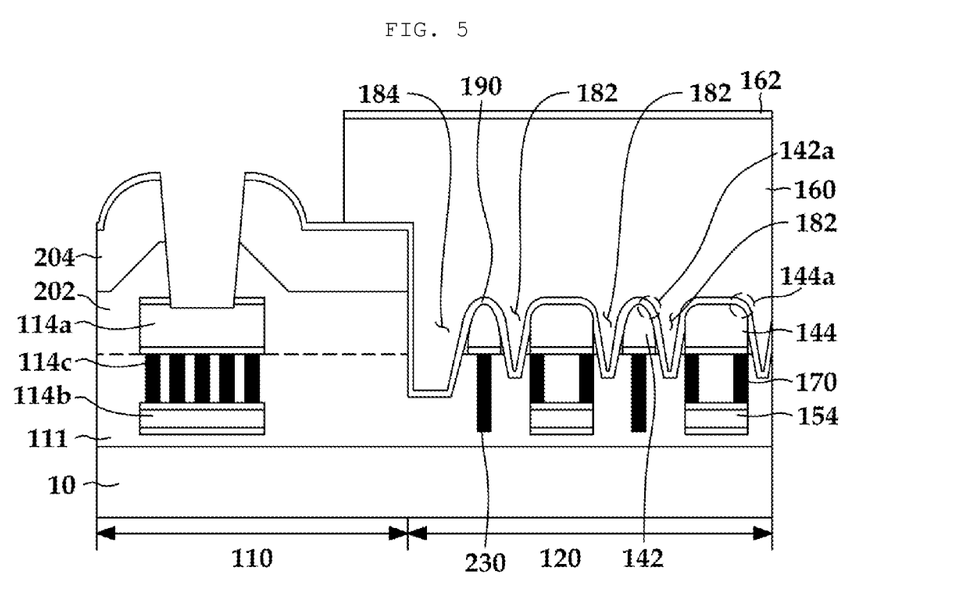
FIG. 5 is a cross-sectional view of another example of a capacitive humidity sensor.

FIG. 5 illustrates a cross-sectional view of a capacitive humidity sensor according to another example. Since various features of the capacitive humidity sensor illustrated in FIG. 5 are similar to the features illustrated in view of FIG. 4H, with like reference numerals designating like features, only different features will be described in detail.

That is, referring to FIG. 5, a via 230 may be formed below the first electrode 142. An example in which the via exists may sufficiently ensure the capacitance changed according to the humidity as compared with an example in which the via does not exist. In addition, the via 230 connected to the first electrode 142 is deeper than the via 170 connected to the second electrode 133. As a result, more capacitance may be ensured. The reason is that the first electrode 142 is further extended by additionally forming the via 230.

Further, layouts of the upper electrode may be variously disposed to improve a humidity sensitive ratio. That is, in the aforementioned example, the upper electrode is described as a layout in which the first electrodes having stripe shapes and the second electrodes between the first electrodes are disposed. However, the humidity sensitive ratio may be increased by varying the electrode layout, and as a result, sensitivity may be improved.

Figure 6:
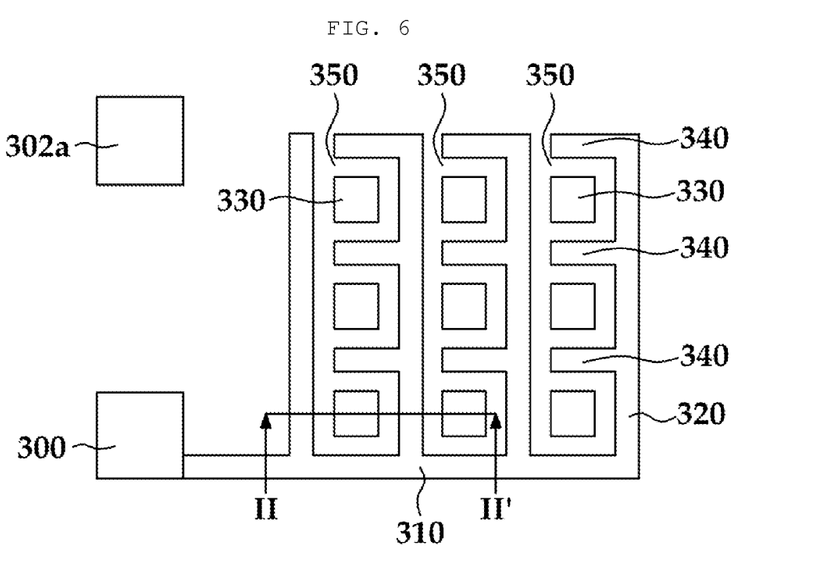
FIG. 6 is a schematic plan view of a modified layout of an upper electrode of yet another example of a capacitive humidity sensor.
Figure 7:
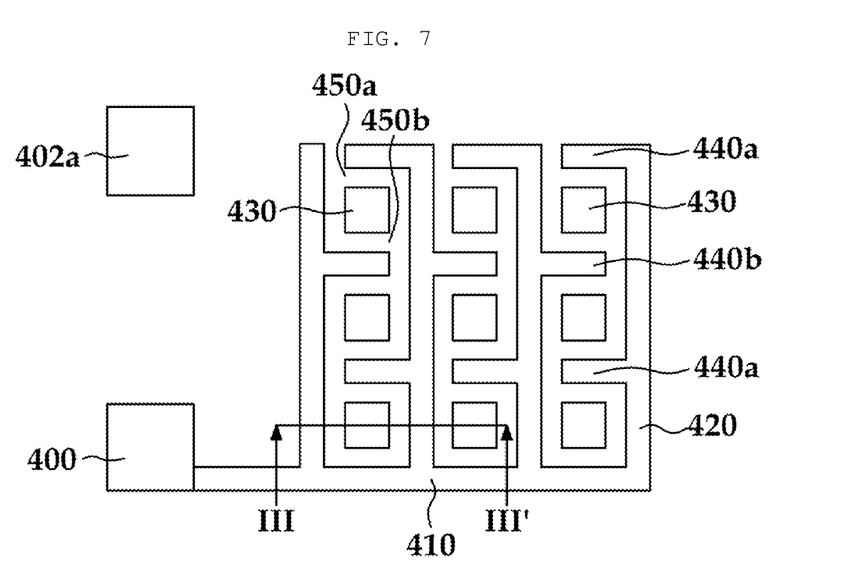
FIG. 7 is a schematic plan view of a modified layout of an upper electrode of yet another example of a capacitive humidity sensor.

Such examples are illustrated in FIGS. 6 and 7. Referring to FIGS. 6 and 7, various features of the illustrated capacitive humidity sensor are similar to the features of the capacitive humidity sensor illustrated in FIG. 1, and only a layout related to the upper electrode will be described in detail.

FIG. 6 is a schematic plan view of a modified layout of an upper electrode of another example of a capacitive humidity sensor.

Referring to FIG. 6, an upper interconnection 310 is connected to a first pad 300. In addition, a plurality of first electrodes 320 is formed in the upper interconnection 310, and second electrodes 330 are disposed between the first electrodes 320. For reference, reference numeral 302a means a second pad connected to a lower interconnection.

In this example, a dummy electrode 340 extended from the first electrode 320 positioned between the second electrodes 330 is further formed in one of the first electrodes 320 facing each other. The dummy electrode 340 is arranged parallel to the upper interconnection 310. In addition, the first electrode 320 and the dummy electrode 340 are the same electrode.

The dummy electrode 340 is formed to open one side 350 so that a region completely surrounding the second electrode 330 is not generated. That is, the first electrode 320 and the dummy electrode 340 do not completely surround the second electrode 330, but are partially open.

FIG. 7 is a schematic plan view of a modified layout of an upper electrode of a capacitive humidity sensor according to another example.

In this example, as in the example illustrated in FIG. 6, a plurality of first electrodes 420 is formed in an upper interconnection 410 connected to a first pad 400 in an orthogonal direction, second electrodes 430 are disposed between the first electrodes 420, and dummy electrodes 440a and 440b extended from the first electrode 420 are formed. For reference, reference numeral 402a means a second pad connected to a lower interconnection.

However, the dummy electrodes 440a and 440b positioned between the second electrodes 430 are extended from different first electrodes 420 to have a zigzag shape. That is, the dummy electrodes 440a and 440b protrude in alternating directions. As a result, diagonal directions 450a and 450b among the region surrounding the second electrode 430 are open.

Meanwhile, as in FIGS. 6 and 7, when the shape of the upper electrode is deformed, in the upper electrodes, that is, dummy electrode 340 of FIG. 6 and dummy electrode 440 of FIG. 7, an area that contacts the humidity sensitive layer existing around the second electrodes 330 and 430 is further increased. Accordingly, it is easier sense a change of capacitance.

Figure 8:
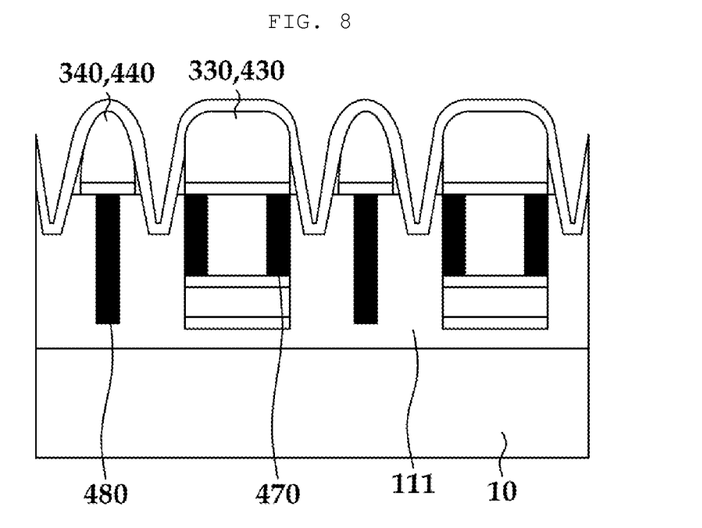
FIG. 8 is a cross-sectional view taken along line II-II' of FIG. 6 and line III-III' of FIG. 7.

FIG. 8 is a cross-sectional view taken along line II-II' of FIG. 6 and line III-III' of FIG. 7.

Referring to FIG. 8, a via 470 is formed below the second electrodes 330 and 430. Selectively, a via 480 may be formed below the first electrodes 340 and 440. In this example, in order to ensure more capacitance, the via 480 has a greater depth than the via 470. Since such a structure may be sufficiently understood through the above-described example, the description thereof will be omitted.

Figure 9:
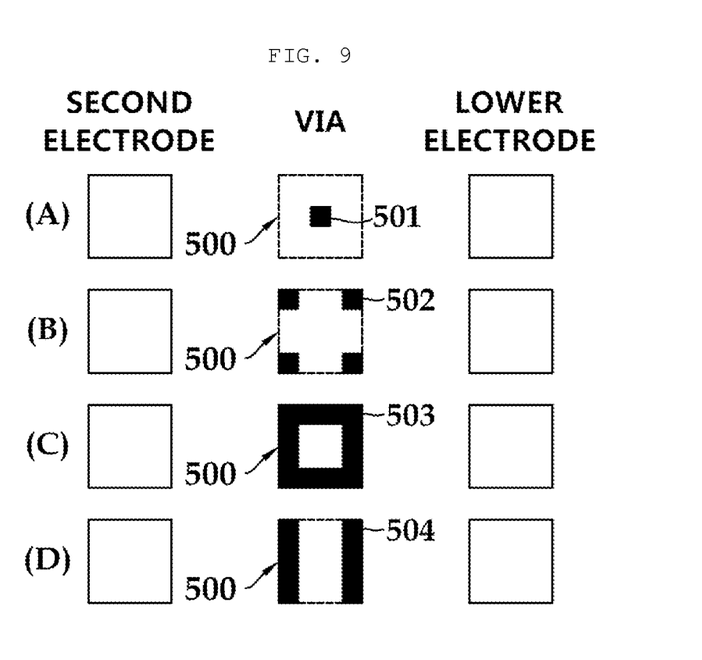
FIG. 9 is a diagram showing various shapes of a via connecting a second electrode and a lower electrode according to various examples.

FIG. 9 is a diagram illustrating various shapes of a via connecting a second electrode and a lower electrode according to various examples of the present disclosure.

FIGS. 9A and 9B illustrate an example in which at least one via is formed between the second electrode and the lower electrode. FIG. 9A illustrates an example in which one via 501 is formed at a center in a via formation region 500 formed between second electrode and the lower electrode, and FIG. 9B illustrates an example in which a via 502 is formed at an edge of the via formation region. Metal such as tungsten is filled in the vias 501 and 502. Of course, other regions corresponding to an insulating layer of the capacitive humidity sensor are made of an insulating material.

FIG. 9C illustrates an example in which a via 503 is formed at the entire edge of the via formation region 500. The insulating material exists in a central region except for the via 503.

In FIG. 9D, a via 504 having a line shape is formed only at a side edge of the via formation region 500. Accurately, the side edge becomes an edge of a direction facing the first electrode. Of course, the insulating material exists in a central region except for the via 504.

Like the examples, when the via is formed, the electric field may be evenly distributed. Further, as a cross sectional area of the via increases, sensitivity for the change in humidity may be increased. This is because the via more overlaps with the humidity sensitive layer as the area of the via increases.

As described above, the example above has a basic technical gist in that, by considering the distribution of the electric field around the electrodes, the vicinity of the electrode is formed deeper than the electrode, and as a result, the humidity sensitive material is filled in the vicinity of the electrode, thereby improving sensitivity of the capacitive humidity sensor.

According to an example of a capacitive humidity sensor having the above-described configuration, there may be the following effects.

With the example, during manufacturing of the capacitive humidity sensor, a humidity insensitive material (polymer) may be filled in a groove formed deeper than an upper electrode around the upper electrode. As a result, a humidity sensitive material region may be increased in comparison to other capacitive humidity sensor that does not have such a structure, thereby improving the sensitivity of the humidity sensor.

Further, an electric field below the electrode may be utilized, and an electrode area may be increased by the via, thereby increasing a variation of capacitance according to a change in humidity. Accordingly, even though the region in which the humidity sensitive material is filled is minimized, the sensitivity may be maintained, and a product installed with the humidity sensor may be miniaturized.

In addition, in one example, layouts of the upper electrode are variously modified, and as a result, the sensitivity may be further improved.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A capacitive humidity sensor, comprising:
   an upper electrode disposed on a first plane comprising first electrodes;
   discrete second electrodes disposed on the first plane and between each of a pair of adjacent first electrodes; and
   a humidity sensitive layer disposed between each of a pair of adjacent second electrodes.

2. The capacitive humidity sensor of claim 1, wherein the first electrodes are connected to each other on the first plane and the second electrodes are not connected to each other on the first plane.

3. The capacitive humidity sensor of claim 1, wherein the humidity sensitive layer is filled in a groove disposed deeper than a bottom surface of the upper electrode.

4. The capacitive humidity sensor of claim 1, further comprising a pad region including a first pad connected to the first electrodes and a second pad connected to the second electrode.

5. The capacitive humidity sensor of claim 1, further comprising two or more second electrodes, and a dummy electrode that extends from at least one of the first electrodes and positioned between two adjacent second electrodes.

6. The capacitive humidity sensor of claim 1, wherein an electrode protection layer is disposed on an upper surface of the upper electrode.

7. The capacitive humidity sensor of claim 6, wherein the upper surface of the upper electrode has a curved shape.

8. The capacitive humidity sensor of claim 1, further comprising a lower electrode disposed on a second plane below the first plane, wherein the lower electrode connects to the second electrodes without connecting to the first electrodes.

9. The capacitive humidity sensor of claim 8, further comprising a first via connecting at least one of the second electrodes and the lower electrode.

10. The capacitive humidity sensor of claim 9, further comprising a second via that connects to at least one of the first electrodes.

11. The capacitive humidity sensor of claim 10, wherein a depth of the first via is different from a depth of the second via.

12. A capacitive humidity sensor, comprising:
    an upper interconnection comprising first electrodes and second electrodes disposed on a first plane;
    a lower interconnection disposed on a second plane;
    a lower electrode included in the lower interconnection and connected to the second electrodes; and
    a humidity sensitive layer surrounding the second electrodes,
    wherein the first electrodes are connected to each other on the first plane, and not connected to each other on the second plane, and
    wherein the second electrodes are not connected to each other on the first plane, and connected to each other on the second plane.

13. The capacitive humidity sensor of claim 12, wherein a depth of the humidity sensitive layer is deeper than a depth of the first plane.

14. The capacitive humidity sensor of claim 12, wherein upper surfaces of the first electrode and the second electrode are curved surfaces.

15. The capacitive humidity sensor of claim 12, wherein the depth of the humidity sensitive layer is positioned between the first plane and the second plane.

16. The capacitive humidity sensor of claim 12, wherein the lower electrode connects to the second electrodes without connecting to the first electrodes.

17. A capacitive humidity sensor, comprising:
    an upper electrode disposed on a first plane and comprising two or more first electrodes disposed parallel to each other;
    second electrodes disposed between two adjacent first electrodes and forming a row of discrete second electrodes between two adjacent first electrodes in the first plane;
    a humidity sensitive layer disposed between each of a pair of adjacent second electrodes and between the row of second electrodes and the two adjacent first electrodes.

18. The capacitive humidity sensor of claim 17, further comprising a plurality of dummy electrodes protruding from the two adjacent first electrodes to be disposed between two adjacent second electrodes of the row of second electrodes.

19. The capacitive humidity sensor of claim 17, further comprising:
   a lower electrode disposed on a second plane below the first plane; and
   vias connecting the second electrodes and the lower electrode.

20. The capacitive humidity sensor of claim 17 further comprising a lower electrode disposed on a second plane below the first plane, wherein the lower electrode connects to the second electrodes without connecting to the first electrodes.

* * * * *